(12) United States Patent
Baker, Jr.

(10) Patent No.: US 7,534,212 B2
(45) Date of Patent: May 19, 2009

(54) PULSE OXIMETER WITH ALTERNATE HEART-RATE DETERMINATION

(75) Inventor: Clark R. Baker, Jr., Castro Valley, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 791 days.

(21) Appl. No.: 10/796,566

(22) Filed: Mar. 8, 2004

(65) Prior Publication Data
US 2005/0197552 A1 Sep. 8, 2005

(51) Int. Cl.
*A61B 5/02* (2006.01)

(52) U.S. Cl. .......................... 600/500; 600/324

(58) Field of Classification Search ............ 600/323, 600/511, 485
See application file for complete search history.

(56) References Cited

U.S. PATENT DOCUMENTS

| | | | |
|---|---|---|---|
| 5,365,934 A * | 11/1994 | Leon et al. ................. 600/517 |
| 5,485,847 A * | 1/1996 | Baker, Jr. .................. 600/323 |
| 5,524,631 A * | 6/1996 | Zahorian et al. ............ 600/511 |
| 5,759,157 A * | 6/1998 | Harada et al. .............. 600/494 |
| 6,157,850 A | 12/2000 | Diab et al. |
| 6,178,343 B1 * | 1/2001 | Bindszus et al. ............ 600/323 |
| 6,374,129 B1 * | 4/2002 | Chin et al. ................. 600/322 |
| 6,411,833 B1 | 6/2002 | Baker et al. |
| 6,584,336 B1 * | 6/2003 | Ali et al. ................... 600/323 |
| 2002/0072660 A1 | 6/2002 | Diab et al. |
| 2002/0128544 A1* | 9/2002 | Diab et al. ................. 600/323 |
| 2002/0137994 A1* | 9/2002 | Baker et al. ................ 600/310 |

OTHER PUBLICATIONS

Reuss et al., "Period Domain Analysis in Fetal Pulse Oximetry," Second Joint EMBS-BMES Conference 2002.

* cited by examiner

*Primary Examiner*—Robert L Nasser
*Assistant Examiner*—Karen E Toth

(57) ABSTRACT

A pulse oximeter which determines multiple heart rates, and selects between them based on the metrics of only one of the heart rate calculations. A primary heart rate calculation method is selected, and is used unless its metrics indicate questionable accuracy, in which case an alternative rate calculation is available and is used instead.

20 Claims, 3 Drawing Sheets

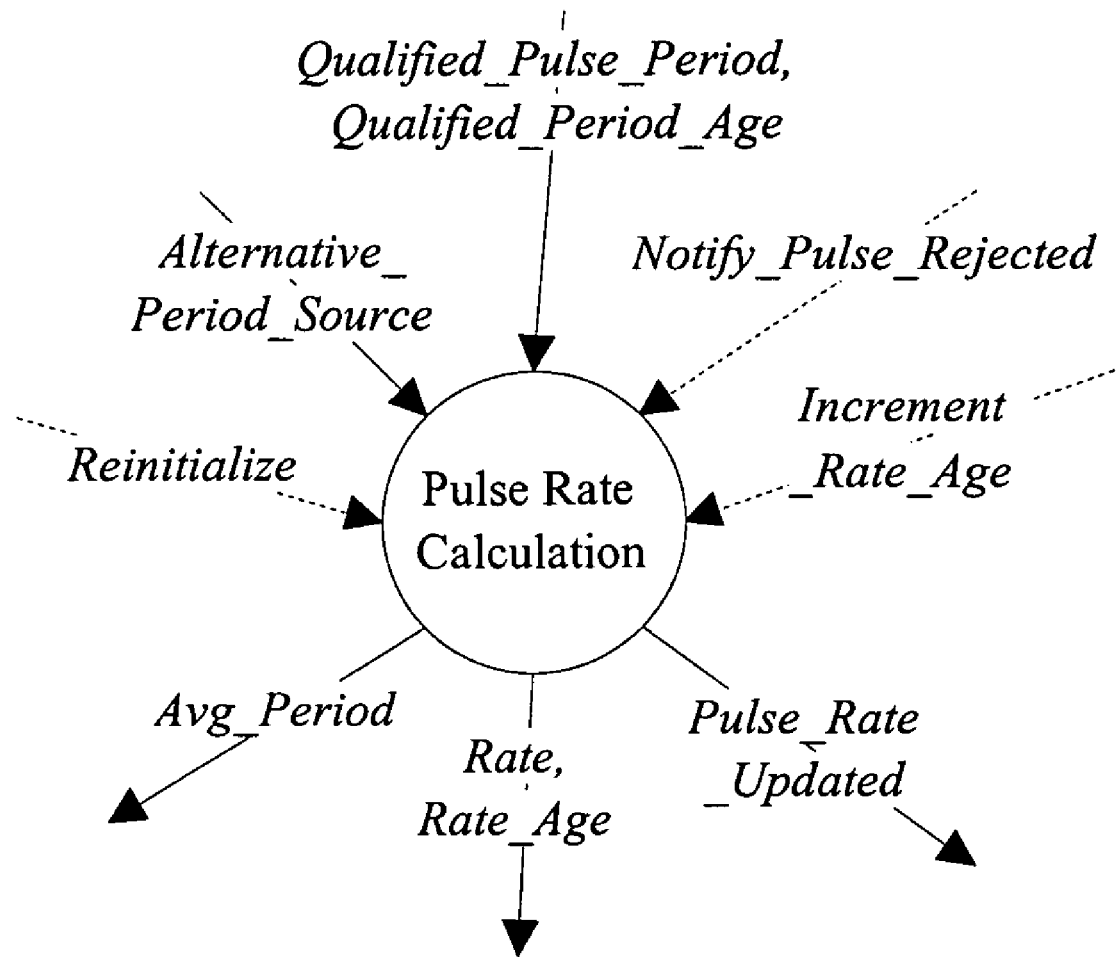
FIG. 3 Context Diagram for Pulse Rate Calculation Subsystem

PULSE OXIMETER WITH ALTERNATE HEART-RATE DETERMINATION

CROSS-REFERENCES TO RELATED APPLICATIONS

Not Applicable

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention relates to oximeters, and in particular to determining a pulse rate by multiple mechanisms in a detected waveform from a pulse oximeter.

Pulse oximetry is typically used to measure various blood chemistry characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed at various wavelengths is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

U.S. Pat. Nos. 6,083,172, 5,853,364 and 6,411,833 show multiple methods of calculating a pulse rate in a pulse oximeter, with a "best rate" module which arbitrates between the pulse rate calculations to select a best rate based on confidence levels associated with each. The confidence levels are calculated using various metrics to determine the reliability of the different pulse rate calculations. Also, U.S. Pat. No. 5,524,631 shows a fetal heart rate monitor that uses multiple parallel filter paths to identify the fetal heart rate, and uses a figure of merit operation to weight the different heart rate estimates.

N-100. The N-100 technology, dating to around 1985, accepted or rejected pulses based on pulse history of the size of pulses, pulse shape, expected time to occur (frequency) and ratio of R/IR.

In particular, the N-100 found pulses by looking for a signal maximum, followed by a point of maximum negative slope, then a minimum. The processing was done in a state machine referred to as "munch." Each maximum was not qualified until the signal passed below a noise threshold, referred to as a noise gate. This acted as an adaptive filter since the noise gate level was set by feedback from a subsequent processing step to adapt to different expected signal amplitudes. The pulses are then accepted or rejected in a "Level3" process which was a filter which adapts to changing signals by comparing the amplitude, period and ratio-of-ratios (ratio of Red to IR, with Red and IR being expressed as a ratio of AC to DC) of a new pulse to the mean of values in a history buffer, then determining if the difference is within a confidence level. If the new pulse was accepted, the history buffer was updated with the values for the new pulse. The level3 process acted as an adaptive bandpass filter with center-frequency and bandwidth (confidence limits) being adapted by feedback from the output of the filter.

N-200. The N-200 improved on the N-100 since it could be synchronized with an ECG, and included ECG filtering. The N-200 also added interpolation to compensate for baseline shift between the time of measuring the pulse maximum and minimum. The N-200 included other filtering features as well, such as a "boxcar" filter which computed the mean of a varying number of signal samples.

The N-200, after various filtering and scaling steps, applies the digitized signals to a "boxcar" filter, which computes the mean of N samples, where N is set by feedback from a subsequent processing step according to the filtered heart rate. New samples are averaged into the boxcar filter, while the oldest samples are dropped. The boxcar length (N) is used to set three parameters: a pulse threshold, absolute minimum pulse and small pulse. An ensemble-averaging (a.k.a "slider") filter then produces a weighted average of the new samples and the previous ensemble-averaged sample from one pulse-period earlier. The samples are then passed to a "munch" state machine and a noise gate, like the N-100. An interpolation feature is added to the N-100 process, to compensate for changes in the baseline level. Since the minimum and maximum occur at different times, a changing baseline may increase or decrease the minimum and not the maximum, or vice-versa.

"Ensemble averaging" is an integral part of C-Lock, which is NELLCOR's trademark for the process of averaging samples from multiple pulses together to form a composite pulse. This process is also known as "cardiac-gated averaging." It requires a "trigger" event to mark the start of each pulse.

BRIEF SUMMARY OF THE INVENTION

The present invention is a pulse oximeter which determines multiple heart rates, and selects between them based on the metrics of only one of the heart rate calculations. A primary heart rate calculation method is selected, and is used unless its metrics indicate questionable accuracy, in which case an alternative rate calculation is available and is used instead.

In one embodiment, the primary heart rate calculation method does not use an ensemble averaged waveform, while the alternative heart rate calculation does use an ensemble averaged waveform. The alternative heart rate calculation is used if the primary calculation has disqualified its most recently detected pulse.

BRIEF DESCRIPTION OF THE DRAWINGS

FIG. 3 is a context diagram of the pulse rate calculation subsystem.

DETAILED DESCRIPTION OF THE INVENTION

Figure 1:
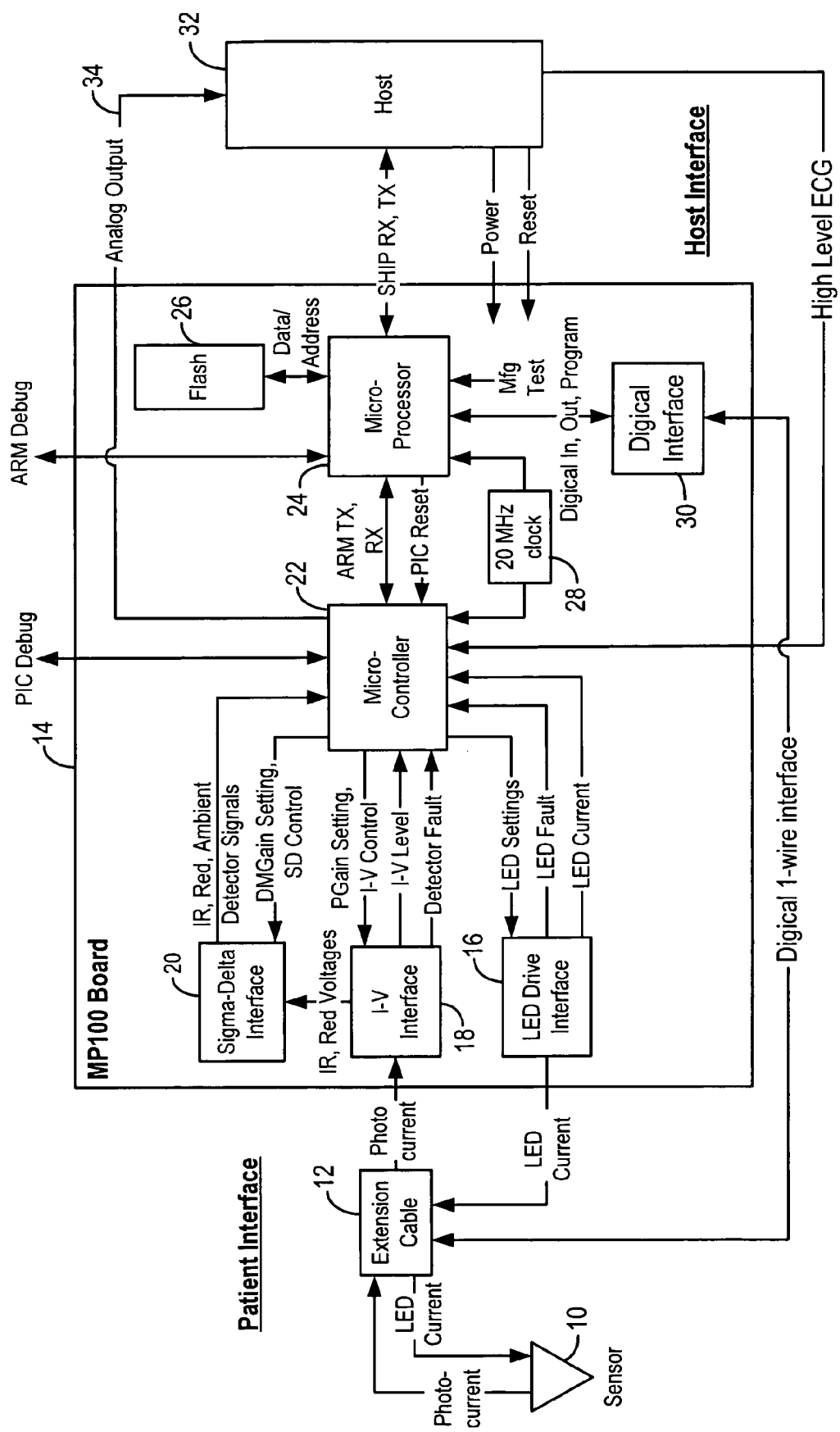
FIG. 1 is a block diagram of an oximetry system incorporating an embodiment of the invention.

FIG. 1 illustrates an embodiment of an oximetry system incorporating the present invention. A sensor 10 includes red and infrared LEDs and a photodetector. These are connected by a cable 12 to a board 14. LED drive current is provided by an LED drive interface 16. The received photocurrent from the sensor is provided to an I-V interface 18. The IR and red voltages are then provided to a sigma-delta interface 20 incorporating the present invention. The output of sigma-delta interface 20 is provided to a microcontroller 22 which includes a 10-bit A/D converter. Controller 22 includes flash memory for a program, and EEPROM memory for data. The processor also includes a controller chip 24 connected to a flash memory 26. Finally, a clock 28 is used and an interface 30 to a digital calibration in the sensor 10 is provided. A separate host 32 receives the processed information, as well as receiving an analog signal on a line 34 for providing an analog display.

Design Summary The design of the present invention is intended to deal with unwanted noise. Signal metrics are measured and used to determine filter weighting. Signal metrics are things that indicate if a pulse is likely a plethysmograph or noise, such as frequency (is it in the range of a human heart rate), shape (is it shaped like a heart pulse), rise time, etc. A similar technique was used in the Nellcor N200, described in the background of this application. The new design adds a number of different features and variations, such as the use of two ensemble averagers as claimed in the present invention.

Figure 2:
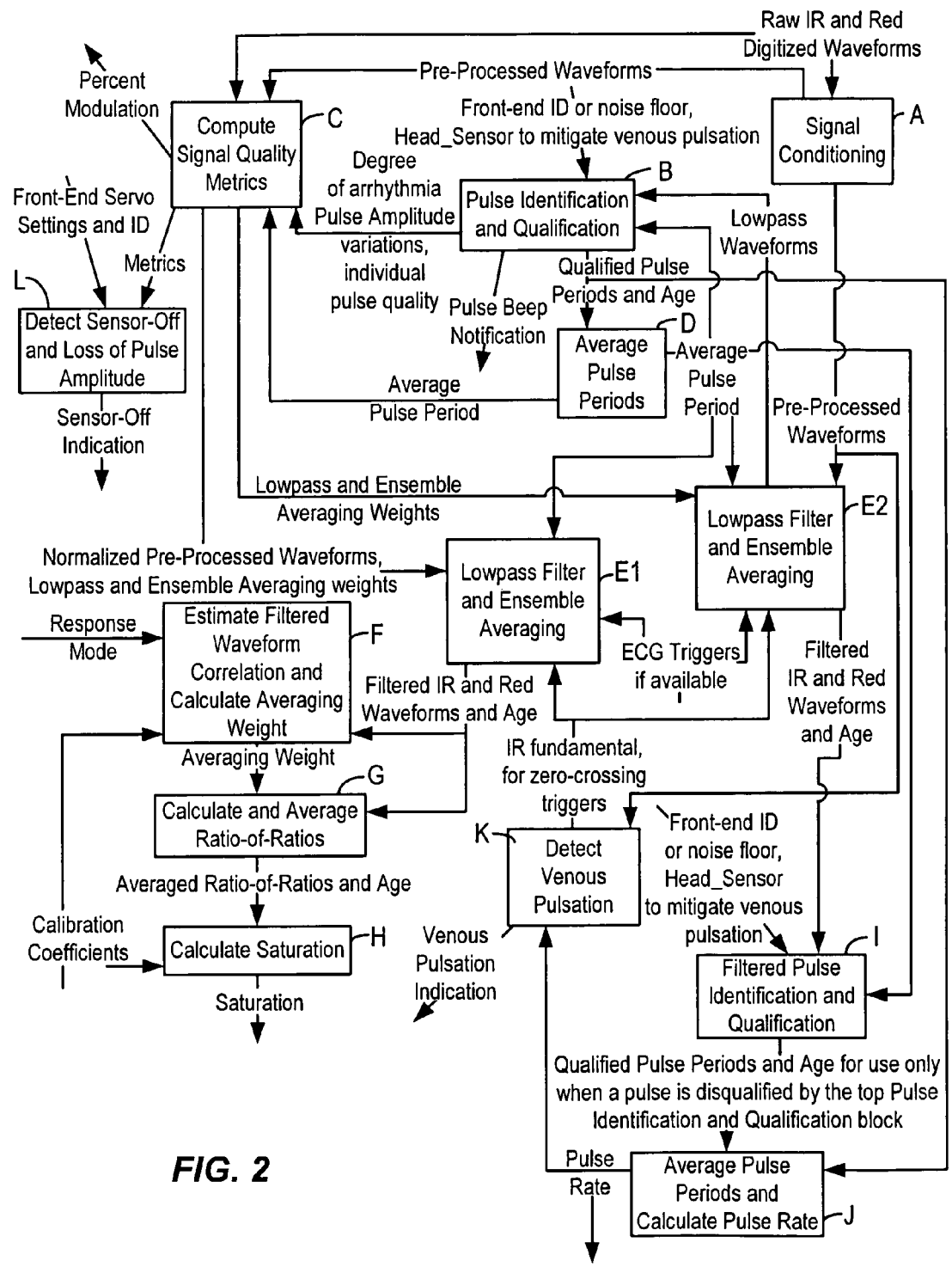
FIG. 2 is a diagram of the software processing blocks of an oximeter including an embodiment of the present invention.

Details of the architecture are shown in the diagram of FIG. 2. This design calculates both the oxygen saturation, and the pulse rate, which are described separately below.

I. Oxygen Saturation Calculation.

A. Signal Conditioning—The digitized red and IR signals are received and are conditioned in this block by (1) taking the 1st derivative to get rid of baseline shift, (2) low pass filtering with fixed coefficients, and (3) dividing by a DC value to preserve the ratio. The function of the Signal Conditioning subsystem is to emphasize the higher frequencies that occur in the human plethysmograph and to attenuate low frequencies in which motion artifact is usually concentrated. The Signal Conditioning subsystem selects its filter coefficients (wide or narrow band) based on hardware characteristics identified during initialization.

Inputs—digitized red and IR signals

Outputs—Pre-processed red and IR signals

B. Pulse Identification and Qualification—The low pass filtered and digitized red and IR signals are provided to this block to identify pulses, and qualify them as likely arterial pulses. This is done using a pre-trained neural net, and is primarily done on the IR signal. The pulse is identified by examining its amplitude, shape and frequency, just as was done in the Nellcor N-100. An input to this block is the average pulse period from block D. This function is similar to the N-100, which changed the upfront qualification using the pulse rate. The output indicates the degree of arrhythmia and individual pulse quality.

Inputs—(1) Pre-processed red and IR signals, (2) Ave. pulse period, (3) Lowpass Waveforms from the low pass filter.

Outputs—(1) Degree of arrhythmia, (2) pulse amplitude variations, (3) individual pulse quality, (4) Pulse beep notification, (5) qualified pulse periods and age.

C. Compute Signal Quality Metrics—This block determines the pulse shape (derivative skew), period variability, pulse amplitude and variability, Ratio of Ratios variability, and frequency content relative to pulse rate.

Inputs—(1) raw digitized red and IR signals, (2) degree of arrhythmia, individual pulse quality, pulse amplitude variation (3) pre-processed red and IR signals, (4) average pulse period.

Outputs—(1) Lowpass and ensemble averaging filter weights, (2) metrics for sensor off detector, (3) Normalized Pre-processed waveforms, (4) percent modulation.

D. Average Pulse Periods. This block calculates the average pulse period from the pulses received.

Inputs—Qualified pulse periods and age.

Outputs—Average pulse period.

E1. Lowpass Filter and Ensemble Averaging—Block E1 low pass filters and ensemble averages the signal conditioned by block A, and normalized by block C, for the pulse rate identification. The weights for the low pass filter are determined by the Signal Metrics block C. The signal is also ensemble averaged (this attenuates frequencies other than those of interest near the pulse rate and its harmonics), with the ensemble averaging filter weights also determined by Signal Metrics block C. Less weight is assigned if the signal is flagged as degraded. More weight is assigned if the signal is flagged as arrhythmic because ensemble-averaging is not appropriate during arrhythmia. Red and IR are processed separately, but with the same filtering weights. The filtering is delayed approximately one second to allow the signal metrics to be calculated first.

The filters use continuously variable weights. If samples are not to be ensemble-averaged, then the weighting for the previous filtered samples is set to zero in the weighted average, and the new samples are still processed through the code. This block tracks the age of the signal—the accumulated amount of filtering (sum of response times and delays in processing). Too old a result will be flagged (if good pulses haven't been detected for awhile).

Inputs—(1) normalized pre-processed red and IR signals, (2) average pulse period, (3) low pass filter weights and ensemble averaging filter weights, (4) ECG triggers, if available, (5) IR fundamental, for zero-crossing triggers.

Outputs—(1) filtered red and IR signals, (2) age.

F. Estimate Filtered Waveform Correlation and Calculate Averaging Weight—this uses a noise metric similar to that used in the N100 and N200 described above, and doesn't use feedback. The variable weighting for the filter is controlled by the ratio-of-ratios variance. The effect of this variable-weight filtering is that the ratio-of-ratios changes slowly as artifact increases and changes quickly as artifact decreases. The subsystem has two response modes. Filtering in the Fast Mode targets an age metric of 3 seconds. The target age is 5 seconds in Normal Mode. In Fast Mode, the minimum weighting of the current value is clipped at a higher level. In other words, a low weight is assigned to the newest ratio-of-ratios calculation if there is noise present, and a high weight if no noise is present.

Inputs—(1) filtered red and IR signals and age, (2) calibration coefficients, (3) response mode (user speed settings).

Outputs—averaging weight for ratio-of-ratios calculation.

H. Calculate Saturation—Saturation is calculated using an algorithm with the calibration coefficients and averaged ratio of ratios.

Inputs—(1) Averaged Ratio-of-Ratios, (2) calibration coefficients.

Outputs—Saturation.

II. Pulse Rate Calculation.

E2. Lowpass Filter and Ensemble Averaging—Block E2 low pass filters and ensemble averages the signal conditioned by block A, for the pulse rate identification. The weights for the low pass filter are determined by the Signal Metrics block C. The signal is also ensemble averaged (this attenuates frequencies other than those of interest near the pulse rate and its harmonics), with the ensemble averaging filter weights also determined by Signal Metrics block C. Less weight is assigned if the signal is flagged as degraded. More weight is assigned if the signal is flagged as arrhythmic since filtering is not appropriate during arrhythmia. Red and IR are processed separately. The process of this block is delayed approximately one second to allow the signal metrics to be calculated first.

The filters use continuously variable weights. If samples are not to be ensemble-averaged, then the weighting for the previous filtered samples is set to zero in the weighted average, and the new samples are still processed through the code. This block tracks the age of the signal—the accumulated amount of filtering (sum of response times and delays in processing). Too old a result will be flagged (if good pulses haven't been detected for awhile).

Inputs—(1) pre-processed red and IR signals, (2) average pulse period, (3) Lowpass filter weights and ensemble averaging filter weights, (4) ECG triggers, if available, (5) IR fundamental, for zero-crossing triggers.

Outputs—(1) filtered red and IR signals, (2) age.

I. Filtered Pulse Identification and Qualification—This block identifies and qualifies pulse periods from the filtered waveforms, and its results are used only when a pulse is disqualified by block B.

Inputs—(1) filtered red and IR signals and age, (2) average pulse period, (3) hardware ID or noise floor, (4) kind of sensor.

Outputs—qualified pulse periods and age.

J. Average Pulse Periods and Calculate Pulse Rate—This block calculates the pulse rate and average pulse period.

Inputs—Qualified pulse periods and age

Outputs—(1) average pulse period, (2) pulse rate.

III. Venous Pulsation

K. Detect Venous Pulsation—Block K receives as inputs the pre-processed red and IR signal and age from Block A, and pulse rate and provides an indication of venous pulsation as an output. This subsystem produces an IR fundamental waveform in the time domain using a single-tooth comb filter which is output to the Ensemble Averaging filters.

Inputs—(1) filtered red and IR signals and age, (2) pulse rate.

Outputs—Venous Pulsation Indication, IR fundamental

IV. Sensor Off

L. Detect Sensor-Off and Loss of Pulse Amplitude—The Pulse Lost and Sensor Off Detection subsystem uses a pre-trained neural net to determine whether the sensor is off the patient. The inputs to the neural net are metrics that quantify several aspects of the behavior of the IR and Red values over the last several seconds. Samples are ignored by many of the oximetry algorithm's subsystems while the Signal State is not either Pulse Present or Sensor Maybe Off. The values of the Signal State variable are: "Pulse Present, Disconnect, Pulse Lost, Sensor Maybe Off, and Sensor Off."

Inputs—(1) metrics, (2) front-end servo settings and ID

Outputs—Signal state including sensor-off indication

Pulse Rate Calculation Subsystem

The subsystem averages qualified pulse periods from the Pulse Identification and Qualification subsystem. It outputs the average period and the corresponding pulse rate.

The oximetry algorithm contains two instances of this subsystem. The first instance receives input from the Pulse Identification and Qualification instance whose input waveform have been processed by the Signal Conditioning subsystem, then lowpass filtered, but not ensemble averaged, by the Ensemble Averaging subsystem. The second instance of the Pulse Rate Calculation subsystem receives input from two instances of the Pulse Identification and Qualification subsystem, the one described above and a second instance that receives input that has been ensemble averaged.

Selection of Pulse Period Source

One instance of the subsystem receives qualified pulse periods from two sources. The subsystem selects which of these two sources to use for its pulse rate calculation based solely on analysis of only one source, the "primary" source. The oximetry algorithm designates the Pulse Identification and Qualification instance that does NOT receive ensemble-averaged waveforms as the primary source, and designates the other Pulse Identification and Qualification instance as the "alternate" source of qualified pulse periods. Qualified pulse periods from the alternate source are only used if the most recent pulse from the primary source was rejected. When a qualified pulse period is received from the primary source, it is always used to update the pulse-rate calculation, and will prevent qualified pulse periods from the alternate source from being used until the primary source once again rejects a pulse period.

Calculation of Average Pulse Period and Pulse-Rate Estimate

When the subsystem uses a Qualified_Pulse_Period, it updates its average pulse period, Avg_Period, using a pulse-based, variable-weight IIR filter, then computes its Rate output from Avg_Period. The steps for this filtering operation are:

$$r_t = (60/\Delta t)/\text{Qualified\_Pulse\_Period} \qquad 1.$$

$$k = \text{Consecutive\_Qualified}/\max(|r_t - r_{t-1}|, |r_{t-1} - r_{t-2}|, |r_{t-2} - r_{t-3}|, 1.0) \qquad 2.$$

$$x = \text{bound}(\min(\text{Avg\_Period}_{t-1}, \text{Qualified\_Pulse\_Period}), \tfrac{3}{4} \text{ seconds}, 2 \text{ seconds})/7 \text{ seconds} \qquad 3.$$

If Rate_Age>10 seconds, $x = \min(x \cdot \text{Rate\_Age}/10 \text{ seconds}, 0.3)$ \qquad 4.

$$k = \max(1/\text{Total\_Qualified}, \min(k, x)) \qquad 5.$$

If $\text{Avg\_Period}_{t-1} < > 0$  $\text{Avg\_Period}_t = \text{Avg\_Period}_{t-1} \cdot (\text{Qualified\_Pulse\_Period}/\text{Avg\_Period}_{t-1})^k$ \qquad 6.

If $\text{Avg\_Period}_{t-1} = 0$
  $\text{Avg\_Period}_t = \text{Qualified\_Pulse\_Period}$ \qquad 7.

$$\text{Rate} = (60/\Delta t)/\text{Avg\_Period}_t \qquad 8.$$

$$\text{Rate\_Age} = \text{Rate\_Age} + k \cdot (\text{Qualified\_Period\_Age} - \text{Rate\_Age}) \qquad 9.$$

where:

$r_t$ is the pulse rate corresponding to Qualified_Pulse_Period, in BPM the $_{t-1}$ subscript denotes the previous qualified pulse.

$\Delta t$ is the oximetry algorithm's sample interval in seconds $60/\Delta t$ is the number of samples per minute x is a filter weight that targets a 7-second response time for typical adult pulse rates.

k is the final filter weight, based on both x and the differences between consecutive values of $r_t$. During the first few pulses, k is increased to at least 1/Total_Qualified so that the initial qualified pulses will be weighted equally.

Consecutive_Qualified is the number of consecutive qualified pulses, and Total_Qualified is the total number of pulses qualified since the subsystem was reinitialized. Both Consecutive_Qualified and Total_Qualified are incremented each time a Qualified_Pulse_Period is used, before k is calculated. Consecutive_Qualified is set to zero when a pulse is rejected by the pulse-period source currently in use.

The update formula for Avg_Period$_t$, in step 6 above, is a geometric average of Avg_Period$_t$, and Qualified_Pulse_Period. Geometric averaging helps to keep the subsystem responsive to large pulses-to-pulse period variations, and large, sustained changes in pulse rate.

Once Rate is initialized to a non-zero value, Rate_Age is incremented every sample, whether or not Rate is updated.

Context Diagram

FIG. 3 is a context diagram of the pulse rate calculation subsystem. The subsystem updates its Avg_Period and Rate outputs from Qualified_Pulse_Periods. It uses Qualified_Pulse_Periods from the Alternative_Period_Source only if it last received a Notify_Pulse_Rejected from the primary source. It updates its Rate_Age output based on Qualified_Period_Age. When Rate is updated, the subsystem sets its Pulse_Rate_Updated flag. The Reinitialize input tells the subsystem to reinitialize itself. Increment_Rate_Age notifies the subsystem to increment its Rate_Age every sample once Rate is initialized.

What is claimed is:

1. A method for determining a heart rate in a pulse oximeter comprising:
    determining a first heart rate from a pulse oximetry signal using a first method;
    determining a second heart rate from the pulse oximetry signal using a second method;
    evaluating a reliability of the first heart rate using metrics applied to the pulse oximetry signal;
    using the first heart rate when the metrics indicate the first method is reliable; and
    using the second heart rate only when the metrics indicate that the first heart rate is unreliable.

2. The method of claim 1 comprising
    determining that the first heart rate is unreliable when the metrics indicate that a most recent pulse is rejected.

3. The method of claim 1 wherein the first method does not use an ensemble averaged waveform, and the second method does use an ensemble averaged waveform.

4. The method of claim 1 wherein determining a first and second heart rate each comprise determining a pulse period, and comprising:
    converting a pulse period used into a rate.

5. The method of claim 4, comprising updating the pulse period using a pulse-based variable-weight filter.

6. A pulse oximeter which determines a heart rate, comprising:
    a first heart rate calculator for determining a first heart rate from a pulse oximetry signal using a first method;
    a second heart rate calculator for determining a second heart rate from the pulse oximetry signal using a second method;
    an evaluator configured to determine the reliability of the first heart rate using metrics applied to the pulse oximetry signal; and
    a selector configured to use the first heart rate when the metrics indicate said first method is reliable, and to use the second heart rate only when the metrics indicate that the first heart rate is unreliable.

7. The pulse oximeter of claim 6, wherein the first heart rate calculator and the second heart rate calculator determine a pulse rate by determining a pulse period.

8. The pulse oximeter of claim 7, wherein the heart rate calculator used for the pulse rate updates the pulse period using a pulse-based variable-weight filter.

9. The pulse oximeter of claim 6, comprising a weighted filter, wherein a filter weight is determined based at least in part on the metrics.

10. The pulse oximeter of claim 6 wherein the selector determines that the first heart rate is unreliable when the metrics indicate that a most recent pulse is rejected.

11. The pulse oximeter of claim 6 wherein the first heart rate calculator does not use an ensemble averaged waveform, and the second heart rate calculator does use an ensemble averaged waveform.

12. A pulse oximetry system comprising:
    a sensor adapted to provide a signal related to a physiological constituent; and
    a monitor adapted to process the signal to determine a pulse period, the monitor comprising:
        software adapted to determine a first pulse period from the signal using a first method;
        software adapted to determine a second pulse period from the signal using a second method;
        an evaluator configured to determine the reliability of the first pulse period using metrics applied to the pulse oximetry signal; and
        a selector configured to use the first pulse period when the metrics indicate the first pulse period is reliable, and to use the second pulse period only when the metrics indicate that the first pulse period is unreliable.

13. The system of claim 12 wherein the first method does not use an ensemble averaged waveform, and the second method does use an ensemble averaged waveform.

14. The system of claim 12 wherein the first pulse period or the second pulse period is converted into a heart rate.

15. The method of claim 1, wherein a filter weight is determined based at least in part on the metrics.

16. A method for determining a heart rate in a pulse oximeter comprising:
    determining a first pulse period from a pulse oximetry signal using a first method;
    evaluating a reliability of the first pulse period using metrics applied to the pulse oximetry signal;
    determining a second pulse period from the pulse oximetry signal using a second method only when the metrics indicate that the first pulse period is unreliable;
    converting the first pulse period into a heart rate when the metrics indicate that the first pulse period is reliable; and
    converting the second pulse period into a heart rate only when the metrics indicate that the first pulse period is unreliable.

17. The method of claim 16 comprising
determining that the first pulse period is unreliable when the metrics indicate that a most recent pulse is rejected.

18. The method of claim 16 wherein the first method does not use an ensemble averaged waveform, and wherein the second method does use an ensemble averaged waveform.

19. The method of claim 16, wherein a filter weight is determined based at least in part on the metrics.

20. The method of claim 16, comprising updating a first pulse period or a second pulse period using a pulse-based variable-weight filter.

* * * * *